United States Patent

Papenfuhs et al.

[11] Patent Number: 5,811,572
[45] Date of Patent: Sep. 22, 1998

[54] PROCESS FOR THE PREPARATION OF N-CARBOXYMETHYLENEANTHRANILIC ACID

[75] Inventors: Theodor Papenfuhs; Andreas Dierdorf, both of Frankfurt; Stefan Krause, Sulzbach/Ts.; Doris Neumann-Grimm, Frankfurt, all of Germany

[73] Assignee: Hoechst Aktiengesellschaft, Frankfurt, Germany

[21] Appl. No.: 797,599

[22] Filed: Feb. 7, 1997

[30] Foreign Application Priority Data

Feb. 9, 1996 [DE] Germany .................. 196 04 707.2

[51] Int. Cl.$^6$ .................................................. C07C 229/00
[52] U.S. Cl. .................................................. 560/44; 560/43
[58] Field of Search ........................................ 560/44, 43

[56] References Cited

U.S. PATENT DOCUMENTS

| | | | |
|---|---|---|---|
| 4,824,995 | 4/1989 | Drysdale | 560/44 |
| 5,686,625 | 11/1997 | Kos | 548/457 |

FOREIGN PATENT DOCUMENTS

| | | | |
|---|---|---|---|
| 0 187 130 | 7/1986 | European Pat. Off. | C07C 99/00 |
| 4403829 | 8/1995 | Germany . | |
| WO 95/18093 | 7/1995 | WIPO . | |

OTHER PUBLICATIONS

*Ullman's Encyclopedia of Industrial Chemistry*, 5th Ed., vol. A14, Editor: Elvers, et al, 1988, pp. 150–151.
Borrione, E., et al, (1988) Synthesis and Cycloaddition Reactions of Ethyl Glyoxylate Imines. Synthesis of Substituted Furo–[3,2–c]quinolines and 7H–Indeno[2,1–c]quinolines, *J. Heterocyclic Chem.* 25: pp. 1831–1835 (1988).
German Official Action.
Derwent Patent Family & Abstract.
Z. Naturforsch, 37b, pp. 1352–1354, Mulbacher, 'Effiziente Synthese von 1–Aryl–4–oxo–azetidin–2–carbonsaureethylester.', 1982.

Primary Examiner—Gary Geist
Assistant Examiner—Brian J. Davis
Attorney, Agent, or Firm—Scott E. Hanf

[57] ABSTRACT

Process for the preparation of N-carboxymethyleneanthranilic acid esters of the formula (3)

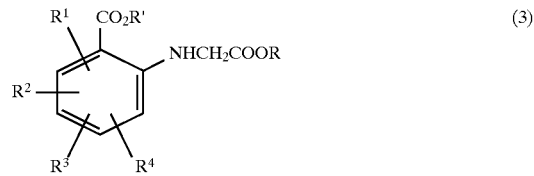

by reacting a compound of the formula (1)

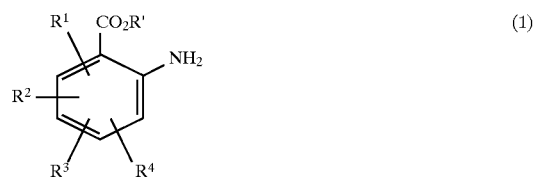

in which R' is hydrogen or a straight-chain or branched alkyl radical having 1 to 4 carbon atoms and $R^1$, $R^2$, $R^3$ and $R^4$ are identical or different and independently of one another are hydrogen, halogen, $NO_2$, a straight-chain or branched alkyl, alkoxy or halogenated alkyl radical having in each case 1 to 6 carbon atoms, with a glyoxylic acid ester of the formula (2)

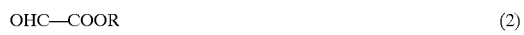

OHC—COOR        (2)

in which R is a straight-chain or branched alkyl radical having 1 to 20 carbon atoms, phenyl radical or benzyl radical, which are unsubstituted or mono- or polysubstituted by halogen or an alkyl or alkoxy group having in each case 1 to 4 carbon atoms, in the presence of a solvent at 0° to 200° C., optionally separating off the water formed during the reaction, and reducing the reaction product with hydrogen in the presence of a hydrogenation catalyst at a temperature of 0° to 200° C. under a pressure of 1 to 150 bar.

19 Claims, No Drawings

PROCESS FOR THE PREPARATION OF N-CARBOXYMETHYLENEANTHRANILIC ACID

The present invention relates to a process for the preparation of N-carboxymethyleneanthranilic acid esters. N-Carboxymethyleneanthranilic acid esters, in particular N-alkoxycarbonyl-methyleneanthranilic acids, are of industrial importance, for example in the preparation of indigo.

According to Ullmann's Encylopedia of Industrial Chemistry, Vol. A14, pages 150 to 151, N-carboxymethyleneanthranilic acid can be prepared by reaction of anthranilic acid with chloroacetic acid. The N-carboxymethyl-eneanthranilic acid can then be esterified with ethanol, using sulfuric acid as a catalyst. A disadvantage of this synthesis is the use of chloroacetic acid, which unavoidably leads to chlorine-containing waste products. However, chlorine-containing waste products are undesirable for environmental protection reasons, and should therefore be avoided. The use of sulfuric acid is furthermore a disadvantage, since acid-containing residues which, like the chlorine-containing waste products, present problems in disposal are formed.

Borrione, Prato, Scorrano, Stivanelli and Lucchini describe, in J. Heterocyclic Chem., 25, 1831 to 1835 (1988), the synthesis of glyoxylic acid ethyl ester-imines and some of their cycloaddition reactions. While anilines with electron-donating groups can be reacted with glyoxylic acid ethyl ester at 25° C. in toluene or methylene chloride without problems to give the corresponding imines, anilines having electron-attracting groups are slow to react and require more severe reaction conditions.

Anilines having electron-donating groups which are investigated are aniline (2a), p-toluidine (2b) and p-methoxyaniline (2c), and anilines having electron-attracting groups which are investigated are p-chloroaniline (2d), p-nitroaniline (2e) and o-nitroaniline. The reaction of the anilines is carried out with glyoxylic acid ethyl ester hydrate in the presence of anhydrous sodium sulfate in toluene (cf. also page 1834, right-hand column: Experimental). The anilines having electron-attracting groups are reacted at 110° C., because of their slowness to react, and give complex reaction mixtures, as demonstrated by NMR monitoring. It is concluded that the complex reaction mixtures obtained by reaction of equimolar amounts of glyoxylic acid ethyl ester and aniline having electron-attracting groups in toluene comprise free imine (anil) and addition products formed by addition of water or unreacted aniline onto the carbon-nitrogen double bond (cf. page 1831, left-hand column, bottom, and right-hand column, top, and right-hand column, last but one paragraph).

The reaction of glyoxylic acid ester with anilines gives imines which are quite unstable and cannot be purified both in the case of anilines having electrondonating groups and in the case of anilines having electron-attracting groups. An attempt to purify the imines by chromatography or distillation leads to substantial decomposition (cf. page 1834, Experimental General Procedure).

J. Heterocyclic Chem., 25, 1831 to 1835 (1988) describes some cycloaddition reactions using the glyoxylic acid ethyl ester-imines, but not the preparation of N-carboxymethyleneanthranilic acid esters.

WO 95/18093 relates to a process for the preparation of N-substituted glycines or glycine esters and the use of the process for the preparation of inidigo. An amine is reacted with a glyoxylic acid ester hemiacetal or glyoxylic acid hemiacetal and the intermediate product formed in this reaction is hydrogenated. The alcohol which has the same alkyl radical as the alkyl part of the particular hemiacetal used is employed as the solvent. The reaction of anthranilic acid methyl ester with glyoxylic acid methyl ester methyl hemi-acetal is described in Example 3 (cf. page 9; Table 1). Both the anthranilic acid methyl ester and the glyoxylic acid methyl ester methyl hemi-acetal are employed —as a solution in a large excess of methanol. The progress of the reaction is monitored by means of thin layer chromatography. When the reaction has ended, the resulting reaction solution is hydrogenated in the presence of a nickel catalyst in a separate step. A disadvantage is the use of methanol as a solvent, since, as a protic solvent, this interferes during further processing of the resulting N-carbomethoxyphenylglycine methyl ester and must therefore be separated off. Furthermore, the use of glyoxylic acid methyl ester methyl hemi-acetal is associated with an additional expenditure, since this hemi-acetal is usually prepared by reaction of glyoxylic acid with methanol. It is also a disadvantage that methanol is unavoidably split off from the hemi-acetal in the course of the reaction, this likewise interfering during further processing, for example during a reaction with phosgene, and therefore having to be removed.

There was therefore a need to provide a process which avoids the abovementioned disadvantages and can furthermore be realized in a simple manner without great technical expenditure. Furthermore, the valuable product is to be obtained in a good yield and at the same time a high purity. Moreover, waste products are to be avoided as far as possible, especially those which are unacceptable from the standpoint of environmental protection.

This object is achieved by a process for the preparation of N-carboxy-methyleneanthranilic acid esters of the formula (3)

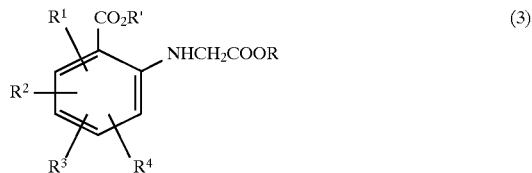

It comprises reacting a compound of the formula (1)

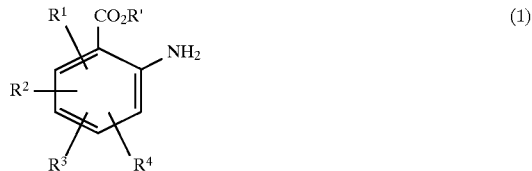

in which R' is hydrogen or a straight-chain or branched alkyl radical having 1 to 4 carbon atoms and $R^1$, $R^2$, $R^3$ and $R^4$ are identical or different and independently of one another are hydrogen, halogen, $NO_2$, a straight-chain or branched alkyl, alkoxy or halogenated alkyl radical having in each case 1 to 6 carbon atoms, with a glyoxylic acid ester of the formula (2)

in which R is a straight-chain or branched alkyl radical having 1 to 20 carbon atoms, phenyl radical or benzyl radical, which are unsubstituted or mono- or polysubstituted by halogen or an alkyl or alkoxy group having in each case 1 to 4 carbon atoms, in the presence of a solvent at 20° to 200° C., optionally separating off the water formed during the reaction, and reducing the reaction product with hydrogen in the presence of a hydrogenation catalyst at a temperature of 0° to 200° C. under a pressure of 1 to 150 bar.

The reaction of the compound of the formula (1) with the glyoxylic acid ester of the formula (2) proceeds via the formation of an imine. The compounds of the formula (1) are anilines which have a $CO_2R'$ group, in which $R'$ is hydrogen or a straight-chain or branched alkyl radical having 1 to 4 carbon atoms. The $CO_2R'$ group is an electron-attracting group, independently of the meaning of $R'$. Both the carboxylic acid group ($R'=H$) and the carboxylic acid ester group ($R'$=alkyl having 1 to 4 carbon atoms) have not only a -J effect but also a -M effect. These two effects demonstrate that the $CO_2R'$ group in compound (1) is an electron-attracting group. In view of the explanation of J. Heterocycl. Chem., 28, 1831 to 1835 (1988), it is to be regarded as surprising that, in spite of their low reactivity and in spite of the low stability and the tendency of their imines formed with glyoxylic acid ester to react with water and unreacted aniline (compound of the formula (1)), anilines having an electron-attracting radical $CO_2$—$R'$ can be converted into the corresponding N-carboxymethyleneanthranilic acid esters by means of the process according to the invention.

It was not to be expected that the reaction proceeds relatively smoothly and requires no excessively severe reaction conditions, and that furthermore the formation of undesirable by-products is kept within limits. It is an advantage that the use of a hemiacetal and the use of an alcohol as the solvent can be omitted, so that an alcohol-free solution of the N-carboxymethyleneanthranilic acid ester enters into the further processing. As a result, undesirable side reactions which are based on the alcohol are avoided.

A compound of the formula (1) in which $R'$ is hydrogen, methyl or ethyl, in particular hydrogen or methyl, preferably hydrogen, is usually employed.

A compound of the formula (1) in which $R^1$, $R^2$, $R^3$ and $R^4$ are identical or different and independently of one another are hydrogen, fluorine, chlorine or an alkyl, alkoxy or chlorine- or fluorine-substituted alkyl radical having in each case 1 to 4 carbon atoms, and in particular $R^1$, $R^2$, $R^3$ and $R^4$ are identical or different and independently of one another are hydrogen, fluorine, chlorine, methyl or ethyl, can be employed in the reaction with good success. Compounds of the formula (1) in which two or three of the radicals, in particular three of the radicals $R^1$, $R^2$, $R^3$ and $R^4$ are hydrogen are of interest. Without making claim to completeness, customary compounds of the formula (1) which may be mentioned are anthranilic acid, anthranilic acid methyl ester, anthranilic acid ethyl ester, 4-chloroanthranilic acid, 4chloroanthranilic acid methyl ester and 4-chloroanthranilic acid ethyl ester, in particular 4-chloroanthranilic acid.

A glyoxylic acid ester of the formula OHC—COOR (2), in which R has the abovementioned meaning, and in particular R is an alkyl radical having 1 to 6 carbon atoms, preferably methyl or ethyl, particularly preferably ethyl, is employed. The reaction of the compound of the formula (1) with the compound of the formula (2) proceeds in the presence of a solvent. Solvents which can be used are an aromatic hydrocarbon, a chlorinated aliphatic or aromatic hydrocarbon, an alkyl ester of an aliphatic carboxylic acid having 1 to 4 carbon atoms, a carboxylic acid amide, an N-containing heterocyclic compound, an ether or an aliphatic carboxylic acid having 1 to 4 carbon atoms, or a mixture thereof, in particular an aromatic hydrocarbon, a chlorinated aromatic hydrocarbon, a carboxylic acid ester or a mixture thereof.

Suitable solvents are, for example, toluene, o-xylene, m-xylene, p-xylene, a mixture of isomeric xylenes, ethylbenzene, mesitylene, chloroform, methylene chloride, chlorobenzene, dichlorobenzene, ethyl acetate, butyl acetate, N, N-dimethylacetamide, N,N-diethylacetamide, N-methylpyrrolidone, tetrahydrofuran, dioxane, diisopropyl ether, di-n-butyl ether, acetic acid, propionic acid or a mixture thereof, in particular toluene, o-xylene, m-xylene, p-xylene, a mixture of isomeric xylenes or ethylbenzene.

Toluene, o-xylene, m-xylene, p-xylene and a mixture of isomeric benzenes have proven to be suitable solvents in many cases.

As already mentioned above, the reaction of the compound of the formula (1) with the compound of the formula (2) is carried out at 0° to 200° C. In a large number of cases, it has proven suitable to allow the reaction to proceed at 10 to 100, in particular 15° to 50° C.

While comparatively reactive compounds of the formula (1) react at low temperatures, for example at 10° to 40° C., the reaction of compounds of the formula (1) which are comparatively slow to react requires higher temperatures, for example 60° C or more. The particular reaction temperature to be used is to be adapted to a certain extent to suit the particular compound of the formula (1) employed, in order to ensure a favorable procedure for the reaction.

Because of their surprisingly marked tendency to decarboxylate, the compounds of the formula (1) in which $R'=H$ (i.e. the anthranilic acids) are to be reacted under mild conditions. It is therefore advisable to react them at 0 to 50, in particular 10 to 40, preferably 15° to 35° C.

The anthranilic acid esters —i.e. the compounds of the formula (1) in which $R'$ is a straight-chain or branched alkyl radical having 1 to 4 carbon atoms —show a low tendency to decarboxylate. They can therefore also be reacted at higher temperatures, for example at 50° C. or more. In a number of cases, they can be reacted under the mild conditions mentioned for anthranilic acid.

In carrying out the reaction at low temperatures (<50° C), it has proven appropriate to heat the glyoxylic acid ester solution at >100° C. for some hours before use, in order to split polymeric constituents into monomeric glyoxylic acid esters. The process according to the invention proceeds in two stages. In the first stage, the addition product is formed from the anthranilic acid or from the anthranilic acid ester of the formula (1) and the glyoxylic acid ester (2). It can be assumed that the corresponding imine is formed and water is split off at the same time. This addition product is reduced with hydrogen in the second stage, the corresponding N-carboxymethyleneanthranilic acid ester of the formula (3) being produced.

The process can be designed flexibly in respect of the water of reaction which arises. In particular, it is possible to omit removal of the water of reaction and to leave it in the reaction mixture. In this case, reduction of the addition product follows the first stage directly, without removing the water of reaction beforehand. As a result, a separate working step is advantageously dispensed with.

However, it is also possible for the water of reaction resulting from the reaction in the first stage to be removed. The water formed during the reaction is usually separated off by means of azeotropic distillation, by means of a water-binding agent or by means of phase separation, or by a combination of these methods. Examples of suitable dehydrating agents are anhydrous sodium sulfate, calcium chloride or a molecular sieve.

In a number of cases, an azeotropic distillation or a phase separation or a combination of these two methods will be preferred for separating off the water. Azeotropic distillation has often proved to be particularly suitable for separating off the water, in particular already during the reaction. It is particularly simple here for the water to be distilled off azeotropically at the rate at which it is formed during the reaction. In this case, the reaction is carried out at the boiling point of the solvent employed.

However, the water can also be separated off after the reduction carried out in the second stage, in which case the same procedure as described above for separating off the water after the first stage can be followed.

As already mentioned above, the reduction is carried out in the presence of a hydrogenation catalyst at a temperature of 0° to 200° C. under a pressure of 1 to 150 bar, in particular at a temperature of 10° to 100° C., in particular 15° to 50° C., under a pressure of 5 to 60, in particular 15 to 25 bar.

Since the reaction products of the compounds of the formula (1) in which R' is H (i.e. those of the anthranilic acids) with the glyoxylic acid ester of the formula (2) also tend to decarboxylate, the hydrogenation of these imines is carried out under mild conditions, for example at 0 to 50, in particular 10 to 40, preferably 15° to 35° C.

Since the reaction products of the compounds of the formula (1) in which R' is a straight-chain or branched alkyl radical (i.e. those of the anthranilic acid esters) with the glyoxylic acid ester of the formula (2) show a low tendency to decarboxylate, they can indeed also be hydrogenated under the abovementioned mild conditions, but also at higher temperatures, for example at 50° C. or more.

Hydrogenation catalysts which can usually be used are those which are employed in the preparation of amines by aminating hydrogenation. These hydrogenation catalysts usually comprise nickel, cobalt, platinum, palladium, rhodium or ruthenium or compounds of these metals. In a number of cases, a catalyst comprising nickel, platinum, palladium or compounds of these metals is employed as the hydrogenation catalyst.

The hydrogenation catalyst can comprise suitable activators and promoters. It can be support-free or located on a support.

Examples of support-free catalysts are Raney nickel, Raney cobalt, Raney platinum and Raney palladium.

$Al_2O_3$, alumina, silicic acid, silica gel, $SO_2$, kieselguhr or active charcoal, in particular $Al_2O_3$, kieselguhr or active charcoal, are possible as the support material. However, mixtures of these substances can also be used as the support material. The hydrogenation-active metal or the metal compound can be applied to the support material by impregnation or precipitation.

Nickel-comprising supported catalysts based on alumina, silicic acid, silica gel, $SiO_2$, kieselguhr or mixtures thereof, in particular silicic acid, silica gel, kieselguhr or mixtures thereof, are particularly suitable.

Supported catalysts based on active charcoal, in particular active charcoal catalysts comprising platinum or palladium, are furthermore suitable.

The catalyst can be used in the form of a suspension or in a form arranged as a fixed bed.

In some cases, it is advisable to employ sulfides of the abovementioned metals or catalysts comprising these sulfides, or to add to the hydrogenation catalysts sulfur or sulfur-containing compounds, for example alkali metal sulfite or dimethyl sulfoxide, or other substances which reduce the activity of the catalyst to a suitable extent, for example quinoline. Sulfided or sulfited catalysts, in particular catalysts comprising platinum or palladium, can also be used for this purpose. These modified catalysts are particularly suitable for allowing the process according to the invention to proceed in one step, i.e. the first and second stage simultaneously, and, if halogen-containing compounds of the formula (1) are used, for suppressing undesirable elimination of the halogen.

The conditions for the reduction also depend on the nature of the catalyst employed. While highly active catalysts, for example catalysts comprising nickel, allow hydrogenation at comparatively low temperatures, the use of less reactive catalysts, for example sulfur-modified catalysts, requires relatively higher reaction temperatures.

If in doubt, the nature and amount of the hydrogenation catalyst should be determined beforehand by means of simple preliminary experiments, in which the choice of solvent is also made.

A particularly favorable process variant comprises introducing the compound of the formula (1), the compound of the formula (2), the solvent, the hydrogenation catalyst and hydrogen together into the reaction vessel and carrying out the reaction and reduction at the same time. In this case, the water is separated off after the reaction has ended. However, it is also possible to remove the water from the circulation during the reaction. Advantageously, however, the water is separated off only after the reaction has ended.

This process variant (one-pot process) is carried out at a temperature of 0 to 200, in particular 10 to 100, preferably 15° to 50° C. under a pressure of 1 to 150, in particular 5 to 60, preferably 15 to 25 bar.

While comparatively reactive compounds of the formula (1) are also reacted at low temperatures, for example at 10° to 40° C., in this process variant, the reaction of compounds of the formula (1) which are comparatively slow to react requires higher temperatures. The same also applies to the reaction products of the compounds of the formula (1) with the glyoxylic acid ester of the formula (2).

Compounds of the formula (1) which tend to decarboxylate —for example, as mentioned above, the anthranilic acids of the formula (1) in which R' is H —and reaction products which readily decarboxylate (imines) are subjected to the reaction which proceeds with splitting off of water and the hydrogenation of the reaction productions (imines) under mild conditions. The compounds of the formula (1) in which R' is H, i.e. the anthranilic acids, for example, are reacted at 0 to 50, in particular 10 to 40, preferably 15° to 35° C., and the hydrogenation of the imines, which proceeds at the same time, is also carried out at this temperature.

On the basis of their low tendency to decarboxylate, anthranilic acid esters, i.e. compounds of the formula (1) in which R' is a straight-chain or branched alkyl radical having 1 to 4 carbon atoms, can be reacted both under the abovementioned mild conditions and at higher temperatures, for example at 50° C. or more. The same also applies to their reaction products (imines), which in a number of cases can be hydrogenated both under the abovementioned mild conditions and at higher temperatures, for example 50° C. or more.

In this process variant, the splitting off of water and the hydrogenation proceed at the same time and the splitting off of water and hydrogenation can be allowed to proceed at one and the same temperature.

The following examples demonstrate the invention without limiting it.

EXPERIMENTAL PART

Example 1

Preparation of N-ethoxycarbonylmethyleneanthranilic acid (two stages)

137 g (1 mol) of anthranilic acid, 204 g of a 50% strength solution of glyoxylic acid ethyl ester in toluene and 400 g of chloroform are initially introduced into a glass flask fitted with a reflux condenser and water separator, and are heated under reflux. The water of reaction obtained is distilled off azeotropically during the reaction and removed from the circulation by means of the water separator. The chloroform obtained by this procedure is recycled into the reaction.

The progress of the reaction is monitored analytically by HPLC (high pressure liquid chromatography). The reaction has ended after about 4 hours. Thereafter, the chloroform is separated off by distillation, the reaction mixture is transferred to a hydrogenating autoclave and 5 g of a palladium-on-active charcoal catalyst (10% by weight of palladium) are added.

Hydrogenation is then carried out at 30° to 40° C. under a hydrogen pressure of 20 bar until the reaction mixture takes up no further hydrogen.

After the catalyst has been filtered off and the solvent has been distilled off, 225 g of crude product which, according to analysis by HPLC, comprises about 90% of N-ethoxycarbonylmethyleneanthranilic acid are obtained.

Example 2
Preparation of N-ethoxycarbonylmethyleneanthranilic acid (one-pot process) 400 ml of toluene are added to 61 g of a 50% strength by weight solution of glyoxylic acid ethyl ester in toluene (corresponding to 0.3 mol of glyoxylic acid ethyl ester) and the mixture is heated under reflux for 5 hours in order to split polymeric constituents into monomeric glyoxylic acid ethyl ester. The solution is then cooled to room temperature.

This glyoxylic acid ethyl ester solution, 35 g (0.25 mol) of anthranilic acid and 2.5 g of a sulfited platinum-on-active charcoal catalyst (5% by weight of Pt) are initially introduced into an autoclave and hydrogenation is carried out at 30° C. under a hydrogen pressure of 20 bar for 8 hours, while stirring. Thereafter, analysis by gas chromatography (GC) indicates complete conversion of the anthranilic acid into N-ethoxycarbonylmethyleneanthranilic acid.

The suspension is filtered, the solid which has been separated off as a result is taken up in 200 ml of ethanol and the mixture is heated under reflux. The suspension obtained as a result is filtered hot and the solvent is distilled off from the filtrate until the valuable product starts to crystallize.

The mixture is cooled to 20° C. and filtered and the solid is dried. 54 g of N-ethoxycarbonylmethyleneanthranilic acid, corresponding to a yield of 80%, based on the anthranilic acid employed, are obtained.

The N-ethoxycarbonylmethyleneanthranilic acid is converted into N-ethoxycarbonylmethyleneanthranilic acid methyl ester by means of diazomethane and is analyzed by mass spectrometry in this form. MS (as methyl ester after reaction with diazomethane) 237 (10), 164 (30), 132 (100), 77 (25)

Example 3
Preparation of 4-chloro-N-ethoxycarbonylmethylene-anthranilic acid (one-pot process)

400 ml of toluene are added to 61 g of a 50% strength by weight solution of glyoxylic acid ethyl ester in toluene (corresponding to 0.3 mol of glyoxylic acid ethyl ester) and the mixture is heated under reflux for 5 hours in order to split polymeric constituents into monomeric glyoxylic acid ethyl ester. The solution is then cooled to room temperature.

This glyoxylic acid ethyl ester solution, 43 g (0.25 mol) of 4-chloroanthranilic acid and 2.5 g of a sulfited platinum-on-active charcoal catalyst (5% by weight of Pt) are initially introduced into an autoclave and hydrogenation is carried out at 30° C. under a hydrogen pressure of 20 bar for 8 hours, while stirring. Thereafter, analysis by gas chromatography (GC) indicates complete conversion of the 4-chloroanthranilic acid into 4-chloro-N-ethoxycarbonylmethylene-anthranilic acid.

The 4-chloro-N-ethoxycarbonylmethylene-anthranilic acid is converted into 4-chloro-N-ethoxycarbonylmethylene-anthranilic acid methyl ester by means of diazomethane and is analyzed by mass spectrometry in this form. MS (as the methyl ester after reaction with diazomethane) 271 (15), 199 (40), 166 (100)

We claim:
1. A process for the preparation of an N-carboxymethyleneanthranilic acid ester of the formula (3)

which comprises reacting a compound of the formula (1)

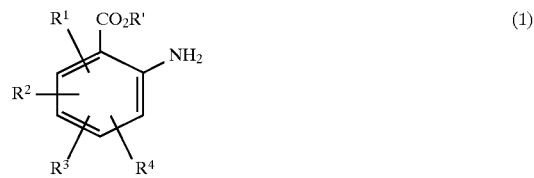

in which R' is hydrogen or a straight-chain or branched alkyl radical having 1 to 4 carbon atoms and $R^1$, $R^2$, $R^3$ and $R^4$ are identical or different and independently of one another are hydrogen, halogen, $NO_2$, a straight-chain or branched alkyl, alkoxy or halogenated alkyl radical having in each case 1 to 6 carbon atoms, with a glyoxylic acid ester of the formula (2)

in which R is a straight-chain or branched alkyl radical having 1 to 20 carbon atoms, phenyl radical or benzyl radical, which are unsubstituted or mono- or polysubstituted by halogen or an alkyl or alkoxy group having in each case 1 to 4 carbon atoms, in the presence of a solvent at 0° to 200 ° C., optionally separating off the water formed during the reaction, and reducing the reaction product with hydrogen in the presence of a hydrogenation catalyst at a temperature of 0° to 200° C. under a pressure of 1 to 150 bar.

2. The process as claimed in claim 1, wherein R' is hydrogen, methyl or ethyl.

3. The process as claimed in claim 1, wherein, R' is hydrogen.

4. The process as claimed in claim 1, wherein $R^1$, $R^2$, $R^3$ and $R^4$ are identical or different and independently of one another are hydrogen, fluorine, chlorine $C_1$–$C_4$-alkyl, $C_1$–$C_4$-alkoxy or chlorine or fluorine-substituted alkyl radical having 1 to 4 carbon atoms.

5. The process as claimed in claim 1, wherein $R^1$, $R^2$, $R^3$ and $R^4$ are identical or different and independently of one another are hydrogen, fluorine, chlorine, methyl or ethyl.

6. The process as claimed in claim 1, wherein two or three of the radicals $R^1$, $R^2$, $R^3$ and $R^4$ are hydrogen.

7. The process as claimed in claim 1, wherein formula 1 is 4-chloroanthranilic acid.

8. The process as claimed in claim 1, wherein R is an alkyl radical having 1 to 6 carbon atoms.

9. The process as claimed in claim 1, wherein R is methhyl or ethyl.

10. The process as claimed in claim 1, wherein R is ethyl.

11. The process as claimed in claim 1, wherein said solvent is an aromatic hydrocarbon, a chlorinated aliphatic or aromatic hydrocarbon, an alkyl ester of an aliphatic carboxylic acid having 1 to 4 carbon atoms, a carboxylic acid amide, an N-containing heterocyclic compound, an ether or a mixture thereof.

12. The process as claimed in claim 1, wherein said solvent is toluene, o-xylene, m-xylene, p-xylene, a mixture of isomeric xylenes, ethylbenzene, mesitylene, chloroform, methylene chloride, chlorobenzene, dichlorobenzene, ethyl acetate, butyl acetate, N,N-dimethylacetamide, N,N-diethylacetamide, N-methylpyrrolidone, tetrahydrofuaran, dioxane, diisopropyl ether, di-n-butyl ether or a mixture thereof.

13. The process as claimed in claim 1, wherein the reaction is carried out at a temperature from 10° to 100° C.

14. The process as claimed in claim 1, wherein the water formed during the reaction is separated off by means of azeotropic distillation, by means of a water-binding agent or by means of phase separation.

15. The process as claimed in claim 1, wherein said hydrogenation catalyst comprises nickel, cobalt, platinum, palladium, rhodium, ruthenium or compounds of these metals.

16. The process as claimed in claim 1, wherein the reduction is carried out at a temperature from 10 to 100.

17. The process as claimed in claim 1, wherein the compound of the formula (1), the compound of the formula (2), the solvent, the hydrogenation catalyst and hydrogen are introduced into the reaction vessel together and the reaction and the reduction are carried out at the same time.

18. The process as claimed in claim 13, wherein the reaction is carried out, at a temperature from 15° to 50° C.

19. The process as claimed 16, wherein the reduction is carried out at a temperature from 15° to 50° C.

* * * * *